US009933397B2

(12) United States Patent
Maev et al.

(10) Patent No.: US 9,933,397 B2
(45) Date of Patent: Apr. 3, 2018

(54) METHOD AND SYSTEM FOR ASSESSING THE QUALITY OF ADHESIVELY BONDED JOINTS USING ULTRASONIC WAVES

(71) Applicant: Tessonics Corp., Birmingham, MI (US)

(72) Inventors: Roman Grigorievich Maev, Windsor (CA); Sergey Aleksandrovich Titov, Moscow (RU); Alexey Nikolaevich Bogachenkov, Moscow (RU)

(73) Assignee: Tessonics Corp., Birmingham, MI (US)

( * ) Notice: Subject to any disclaimer, the term of this patent is extended or adjusted under 35 U.S.C. 154(b) by 644 days.

(21) Appl. No.: 13/862,937

(22) Filed: Apr. 15, 2013

(65) Prior Publication Data

US 2013/0289895 A1 Oct. 31, 2013

Related U.S. Application Data

(60) Provisional application No. 61/623,838, filed on Apr. 13, 2012.

(51) Int. Cl.
| | |
|---|---|
| *G01B 5/28* | (2006.01) |
| *G01N 3/32* | (2006.01) |
| *G01N 29/04* | (2006.01) |
| *G01N 29/44* | (2006.01) |
| *G01N 29/30* | (2006.01) |

(52) U.S. Cl.
CPC ......... *G01N 29/4436* (2013.01); *G01N 29/30* (2013.01); *G01N 2291/0289* (2013.01); *G01N 2291/044* (2013.01); *G01N 2291/051* (2013.01)

(58) Field of Classification Search
CPC ... G01N 2291/0234; G01N 2291/2672; G01N 29/069; G01N 29/11
USPC .................. 702/35, 39; 73/584, 588, 600
See application file for complete search history.

(56) References Cited

U.S. PATENT DOCUMENTS

| | | | | |
|---|---|---|---|---|
| 4,184,373 A | | 1/1980 | Evans et al. | |
| 8,215,173 B2* | | 7/2012 | Spencer | G01N 29/069 73/620 |
| 2008/0151690 A1* | | 6/2008 | Tang | G01V 1/44 367/35 |

(Continued)

OTHER PUBLICATIONS

International Preliminary Report on Patentability for PCT Application No. PCT/US2013/036576, dated Oct. 23, 2014.

(Continued)

*Primary Examiner* — An Do
(74) *Attorney, Agent, or Firm* — Carlson, Gaskey & Olds, P.C.

(57) ABSTRACT

A method is provided for assessment of quality of an adhesively-bonded lap joint, wherein the joint includes a first metal plate, a second metal plate and an adhesive therebetween. The method includes sending ultrasonic waves normally to the surface of a sample outside of the joint where the sample has a first sample metal plate with the same properties as does the first metal plate at an assessment point of the joint. Reflected waves from the sample joint as a reference waveform are recorded. Wideband ultrasonic waves are sent normally to the surface of the joint at the assessment point. Reflected waves of the ultrasonic waves from the joint are recorded. A waveform of the reflected waves from the joint and reference waveform are analyzed to determine an informative parameter. The informative parameter is compared with a threshold value to assess quality of the joint.

10 Claims, 8 Drawing Sheets

(56) References Cited

U.S. PATENT DOCUMENTS

| | | |
|---|---|---|
| 2009/0277270 A1 | 11/2009 | Huebler et al. |
| 2010/0031750 A1 | 2/2010 | Spencer et al. |
| 2011/0181300 A1* | 7/2011 | Bowring ................ G01S 7/411 |
| | | 324/637 |

OTHER PUBLICATIONS

Titov et al., "Pulse-echo NDT of Adhesively Bonded Joints in Automotive Assemblies," Ultrasonics, IPC Science and Technology Press Ltd., Guildford, GB, vol. 48, No. 6-7, Nov. 1, 2008, pp. 537-546.

International Search Report and Written Opinion for PCT Application No. PCT/US2013/036576, dated Jul. 10, 2013.

* cited by examiner

METHOD AND SYSTEM FOR ASSESSING THE QUALITY OF ADHESIVELY BONDED JOINTS USING ULTRASONIC WAVES

BACKGROUND

The invention is related to the non-destructive testing (NDT) of adhesively-bonded joints which consist of two plates, usually made of metal and adhesive layer between them. For example, the adhesive joints are assembled with sheets of steel or, in some cases, aluminium sheets. The typical thicknesses of these materials are in the range of 0.7-2 mm. During the manufacturing process, adhesives or sealants are typically applied between these sheets prior to the formation of complex joints by means of spot welds, rivets or clinch flanges. Naturally, during the formation process, large forces are applied to these metals, resulting in the deformation of the mating parts. This gives rise to large-scale variations in the thicknesses of the adhesive layers. In fact, in some regions the thicknesses are often found to be less than 0.1 mm, while in others exceed 1 mm. Furthermore, uncured adhesives tend to accumulate in locations where the gap between adherends is increased, thereby leaving voids in neighbouring regions which remain in the joint even after the curing process is complete. Adhesive joints are therefore highly non-uniform in nature.

Many ultrasonic method have been proposed for testing of the adhesive joints.

Difficulties of the ultrasonic testing of the adhesive joints caused by the impedance mismatch of the materials and signal overlapping. The acoustical impedance mismatch between the adhesive and the metal—especially for steel—produces prolonged, strong reverberations of the wave in the first metal sheet. If the time delays of the wave propagation in the adhesive layer and metal sheet are approximately equal (or a multiple of each other) these reverberations sufficiently mask the small echoes returning from the second adhesive/metal or the adhesive/air interface (furthest from the transducer).

To reduce the impedance mismatch between the transducer and the metal sheet it has been proposed that the contact transducer utilize a wear resistant shoe of high impedance. In this experiment, the reverberations in the metal have been shown to be significantly decreased, enabling the detection of the resonance frequencies of the adhesive layer. However, these measurements were very sensitive to the quality of the acoustical contact. As a result, this technique was only effective when using perfectly flat and smooth surfaces.

Several ultrasonic resonance spectroscopy methods have been proposed for the evaluation of layered structures. For example, bond testers measure the frequency and amplitude of the through-thickness resonances of a system comprised of a probe coupled to the specimen. The changes in these parameters can be used to detect disbonds and voids in the joints and also to assess the condition of the bond. Detection of the defect using narrowband ultrasonic spectroscopy, is based on measurements of the electrical impedance of the transducer, which is dependent on the acoustical impedance of the inspected layered structure. In fact, a dry coupled probe with a rubber delay line has been specially designed for applications within the automotive industry. To improve the lateral resolution of this method, the probe was equipped with a special collimator in effort to narrow the ultrasound beam. Because the mechanical load produced by the delay line on the metal sheet is relatively small, the frequency of the first through thickness resonance of the structure can be readily measured and reliably related to the integrity of the joint.

For all of these techniques, the resonances of typical joints are in the low-frequency range (less than 1 MHz). As such, it is not possible to increase the frequency of ultrasound in effort to achieve better lateral resolution.

It may, however, be possible to obtain a higher resolution by employing a common pulse-echo mode. It has been proposed that disbonds at the first interface can be detected by measuring the decay rate of the reverberations in the first metal sheet. The existence of a disbond slightly increases the reflection coefficient of the ultrasonic wave at the metal/adhesive interface and hence the reverberations should decay faster in the case of good contact between the metal and adhesive. Disbonds at the second adhesive/metal interface on the other hand can be detected through phase inversion of the wave that is reflected from this interface. To reduce the amplitudes of the reverberations in the first sheet and subsequently detect the phase of this echo, a signal processing algorithm based on adaptive inverse filtering has been developed. In this algorithm, a delayed and attenuated copy of the received waveform is subtracted from the original one. If the time delay is equal to the period of reverberation and the attenuation factor is equal to the reflection coefficient at the first interface, save for the first pulse, reflections from the rear metal interface are suppressed. Thus, the echo reflected from the rear adhesive interface is obtained and its phase can be determined, whereby potential disbonds may be detected. The thickness of the adhesive layer can also be estimated using the time delay between this echo and the first pulse that is reflected from the first metal/adhesive interface. Unfortunately, in the case of thin adhesive layers, these pulses are overlapped, making phase detection quite difficult. Moreover, the inverse procedure requires an exact waveform similarity for successive pulses reverberating in the metal sheet. When strong acoustic beam divergence and mode conversion at the interfaces between the layers are present, this requirement is not satisfied.

SUMMARY

This invention is aimed to determine spatial distribution of the adhesive beneath the front plate and detect defects in the adhesive layer using one-sided access.

The defects detected by the proposed method are: voids (or delamination) at the first plate/adhesive interface; voids (or delamination) at the adhesive/second plate interface; voids (or delamination) inside of the adhesive; and foam-like defect (consists of numerous small air bubbles). The method and system will nondestructively measure the positions and sizes of the adhesive area and defects.

The invention provides testing of the joints with increased spatial resolution in case of variation of thickness of the plates and adhesive layer, some curvature of the surfaces, and non-uniformity of the adhesive.

A method for assessment of quality of adhesively bonded lap joints may include sending wideband ultrasonic waves normally to the surface of the joint and recording the reflected waves. Wideband ultrasonic waves are sent normally to the surface of sample outside of the joint where the first metal sheet has the same properties as at the tested point of the joint, and recording reflected waves as a reference. The waveform reflected from the joint and reference waveform is analyzed to determine an informative parameter. The informative parameter is compared with the threshold value to estimate merit of joint quality.

The informative parameter may be a measure of the deviation of the waveform reflected from the joint and reference waveform. This informative parameter may be compared with the threshold value to determine defect in the joint like: air voids at the first interface (absence of adhesive).

The reference waveform may be multiplied with the exponentially decaying function having specific exponential factor; and their product subtracted from the waveform recorded for the joint. The inversion of the polarity of the difference is an indication of the defect in the joint; like presence such defects could include of air voids inside the adhesive or delamination at the adhesive/second metal sheet interface. The time delay of the pulses in the difference waveform is measured to determine thickness of the adhesive layer.

The time shift may be compensated, overall amplitude variation and variation of the reverberation period of the current waveform caused by bad acoustic contact, improper position of the probe, curvature of the surface and variation in the first plate thickness to match the amplitude and reverberation period of the reference waveform. The correction of the amplitude and time scale of the current waveform is produced using the amplitude and time delay of the first pulse reflected from the back surface of the first plate.

The ultrasonic transducer may have multiple elements sending and receiving ultrasonic waves.

The transducer may be translated manually or robotically along the surface of the joint. The recorded waveforms are processed using reference waveforms recorded previously outside of the joint, and the resulting value is used to generate an image map of the quality merit of the joint (defect sizes and location).

The waveforms recorded as functions of time and spatial coordinate may be high pass filtered over the spatial coordinate. A high level of the irregular output is an indication of non-uniformity of the adhesive distribution (foam-like defect). A high level of the regular output is an evidence of the non-parallelism of the rear surface if the adhesive layer and the first plate.

An apparatus for assessment of quality of adhesively bonded lap joints may include means for generating ultrasound waves, propagating same towards the sample and receiving the reflected waves. This may include a single-element, linear or multi-element ultrasonic probe. A storage memory stores the receiving and reference waveforms. A processor processes the waveforms. A display or other user interface may present the results.

A set of calibration samples may include two metal sheets jointed together with the adhesive which thickness varies gradually along the sample from minimal up to maximal possible value.

These samples (coupons) are used for testing of the apparatus and adjustment of the processor according to the specific properties of materials used in the joint, more specifically: to determine the threshold value of the informative parameter for estimation of merit of joint quality, to determine additional exponential factor of the correction function and estimate relationship between time delay of the pulses reflected from the adhesive/second sheet interface and thickness of the adhesive layer.

A set of calibration samples may include two curved metal sheets jointed together with the adhesive which thickness varies gradually along the sample from minimal up to maximal possible value. The samples are used to estimate the changes of the outputs of the processing algorithm caused by the curvature of the specimen under the test and to adjust the processing to compensate for this curvature.

DESCRIPTION OF A PREFERRED EMBODIMENT

Figure 1:
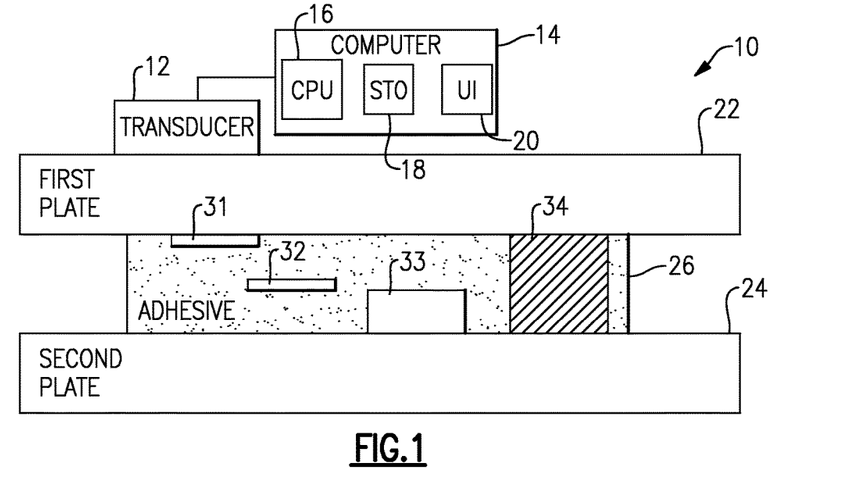
FIG. 1 shows a schematic of the adhesive joint and ultrasonic transducer with defects in the adhesive joint.

FIG. 1 shows a schematic of a system 10 according to one embodiment of the present invention. The system 10 includes a transducer 12 connected to a computer 14 having a CPU 16, storage 18 (such as memory, RAM, hard drives, or some combination of working memory and mass storage, in electronic and/or optical, magnetic or other format). The computer 14 may have a user interface 20 (graphical user interface, input devices, display, etc).

The adhesive joint being measured includes a first plate 22, a second plate 24 (generally parallel to and spaced from the first plate 22) and an adhesive 26 between the first plate 22 and the second plate 24. The typical thicknesses of these materials are in the range of 0.7-2 mm.

FIG. 1 also shows the defects in the adhesive joint i.e. voids 31, 32, 33 and a foam-like defect 34. The defects detected by the proposed method are: voids (or delamination) 31 at the first plate/adhesive interface; voids (or delamination) 32 inside of the adhesive; voids (or delamination) 33 at the adhesive/second plate interface; and foam-like defect 34 (consists of numerous small air bubbles).

There are two approaches of the testing procedure provided by the system 10. The first approach is applicable in the case when the interfaces of the adhesive 26 can be approximated within the transverse dimension of the interrogating ultrasonic beam with planes which are parallel to the surfaces of the plates 22, 24. The second approach is applicable in the case when the adhesive 26 has highly non-flat adhesive/air interface within the transverse dimension of the interrogating ultrasonic beam (foam-like defect) or adhesive has approximately flat interface inclined with respect to the surfaces of the plates 22, 24 or when the first and second plates 22, 24 are not parallel.

First Approach.

Figure 2:
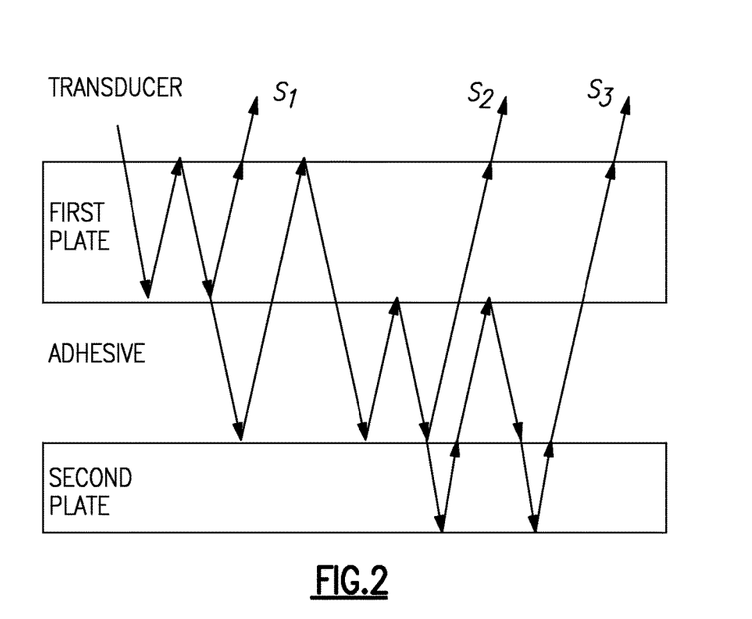
FIG. 2 is a schematic of the acoustic wave propagation in adhesively bonded joint.

In this case the wave propagation can be explained by the model presented in FIG. 2. In this model the interfaces between transducer 12, plates 22, 24 and adhesive 26 are parallel and the ultrasonic wave experiences multiple reverberations within the layers and transitions the interfaces between them. In the waveform received by the transducer in pulse-echo mode it is possible to select the responses S1, S2, S3. Response S1 is completely produced by the waves reverberating in the first plate 22. There is only response S1 when the transducer 12 is located over "no adhesive" area or the defect 31 is presented.

The responses S2 and S3 are produced by the waves which propagate in first metal sheet 22 and adhesive layer 26 and in all three layers, respectively. FIG. 2 shows scheme of the wave propagation. The amplitude of S1 is much larger than the amplitudes of S2 and S3.

The time shift of these responses and reverberation periods depends on the thicknesses of the layers and sound velocities in the plates 22, 24 and the adhesive 26. Since the thicknesses of the layer can have arbitrary values, responses are overlapped in time and generally it is not simple to distinguish them in the output waveform:

$$s(t)=s_1(t)+s_2(t)+s_3(t).$$

Figure 3:
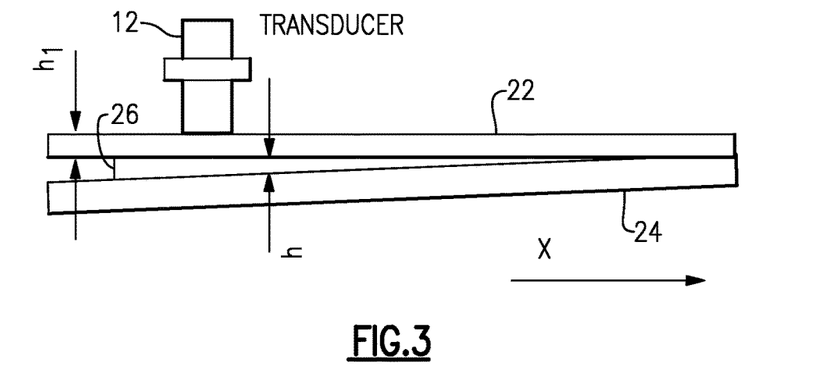
FIG. 3 is a sample with gradually varying adhesive thickness.
Figure 4:
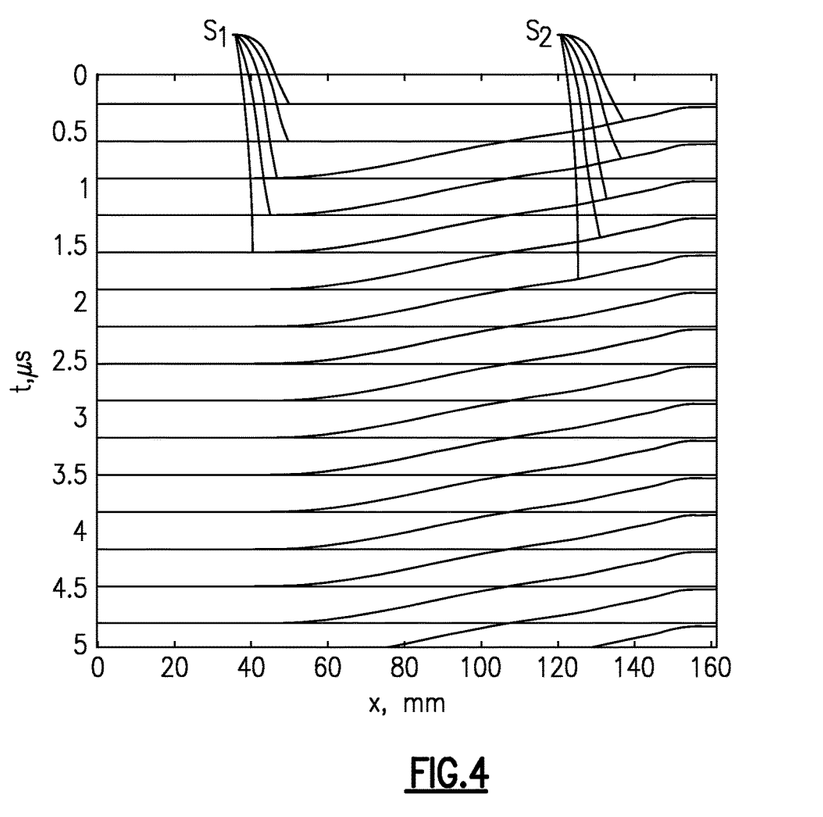
FIG. 4 shows the delays of the responses $S_1$ and $S_2$ recorded for the sample shown in FIG. 3.

However in some special case it is possible to observe these responses separately. FIG. 3 shows sample with gradually varying thickness of the adhesive h(x). FIG. 4 shows the delays of the responses $S_1$ and $S_2$ recorded as a function of position of the transducer x. Since responses S1 and S2 delayed on time which is proportional to the varying thickness of the adhesive layer, they look in the image as tilted lines.

For defect #1 ("no adhesive" area) the responses S2 and S3 are absent and there is the response S1 only.

The responses S2 and S3 are presented in cases of a good joint and in presence of the defects 32 and 33. To distinguish the defects 32 and 33 and good joint, the response S2 should at least be separated.

In case of the foam-like defect 34 the response S2 does not have a regular structure.

FIG. 4 shows the delays of the responses $S_1$ and $S_2$ recorded for the sample shown in FIG. 3.

Figure 5:
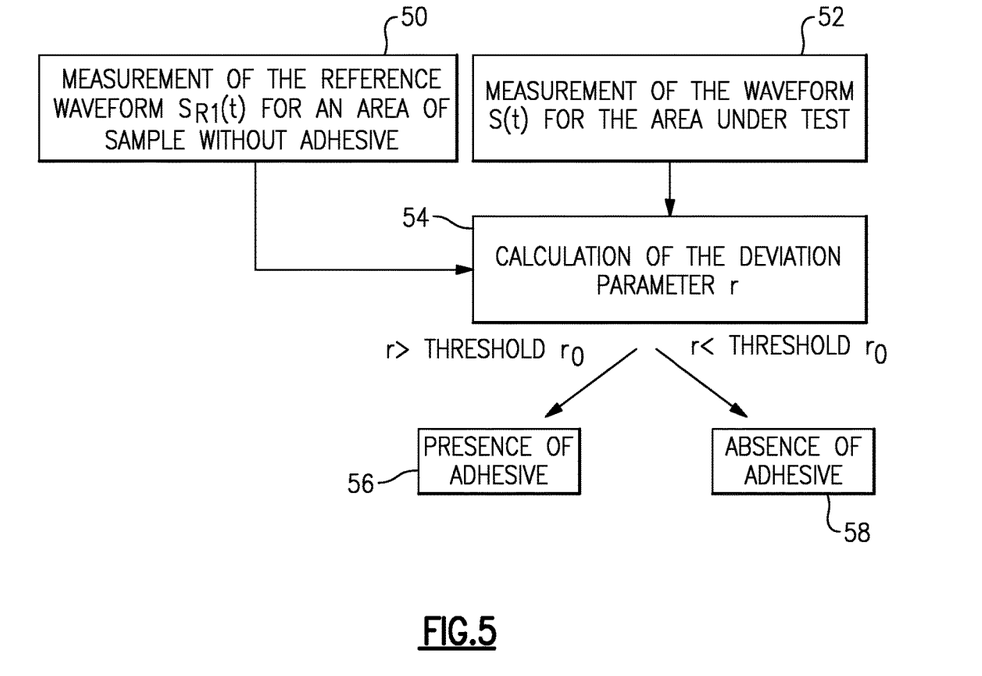
FIG. 5 is a block diagram of the processing.

According to the invention the analysis of the signal is produced as follows and as illustrated by the block scheme presented in FIG. 5. The contact of adhesive 26 with the rear surface of the first plate 22 is tested. This procedure is based on the comparison of the waveform s(t) measured in the point of interest with the previously recorded reference waveform sat) from the outside of the joint for the bare first plate 22. The similarity of the current and reference waveforms can be considered as an evidence of the absence of adhesive 26 in the test point. To compare these measured and reference waveforms the cross correlation coefficient or deviation parameter r can be used. The deviation parameter r is defined as follows:

$$r = \left[ \int_{t_1}^{t_2} (s(t) - s_{R1}(t))^2 \, dt \right]^{1/2}$$

First, in step 50, reference waveform $s_{R1}(t)$ from the outside of the joint for the bare first plate 22 is measured and stored. Then measurement of the waveform s(t) is measured in the point of interest in step 52. Then a deviation parameter is calculated based upon a comparison of the reference waveform and the measured waveform in step 54. Then the deviation parameter should be compared with the threshold $r_0$. If $r>r_0$, the difference between current and reference waveforms is large, then it should be assumed that there is contact with adhesive 26 at the rear surface of the first plate 22 in step 56. If $r<r_0$, the difference between current and reference waveforms is small, then it should be assumed that there is no adhesive 26 at the rear surface of the first plate 22 in step 58.

If the processing presented above shows that there is contact with adhesive at the first interface the second step is to detect defects 32, 33. To do this, the response $s_1(t)$ should be subtracted from the waveform s(t). The response $s_1(t)$ can be measured experimentally using a special calibration specimen which materials are identical to the material of the specimen under the test, the thicknesses of the first plates 22 are equal and the thickness of the adhesive 26 is large enough to be sure that all possible responses S2 and S3 are negligibly small. Alternatively $s_1(t)$ can be estimated by applying additional damping to the reference waveform:

$$s_1(t) \approx s_{R2}(t) = s_{R1}(t) \cdot |R_{12}|^{t/T}$$

where T is the period of the reverberations in the first plate 22. The coefficient $R_{12}$ is the reflection coefficient of the ultrasonic wave at the interface between the first plate 22 and adhesive 26. It can be estimated theoretically using handbook parameters of the materials, and as a result of the experimental calibration procedure.

Figure 6A:
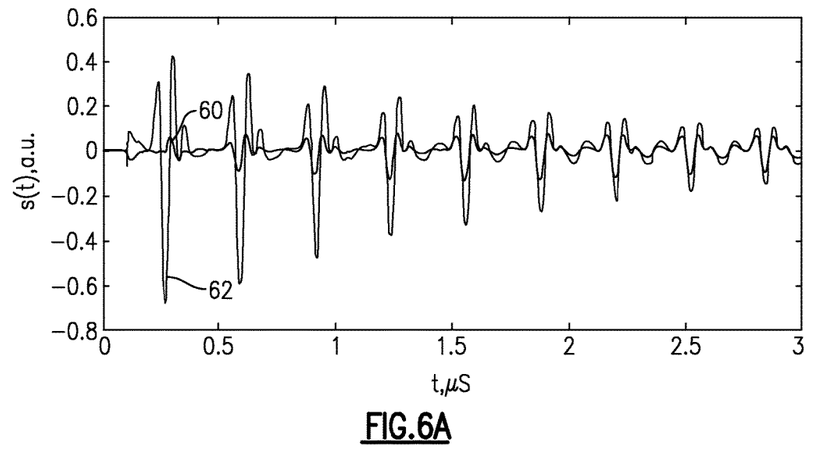
FIG. 6A shows the experimental waveforms (grey curves) measured for the joint.
Figure 6B:
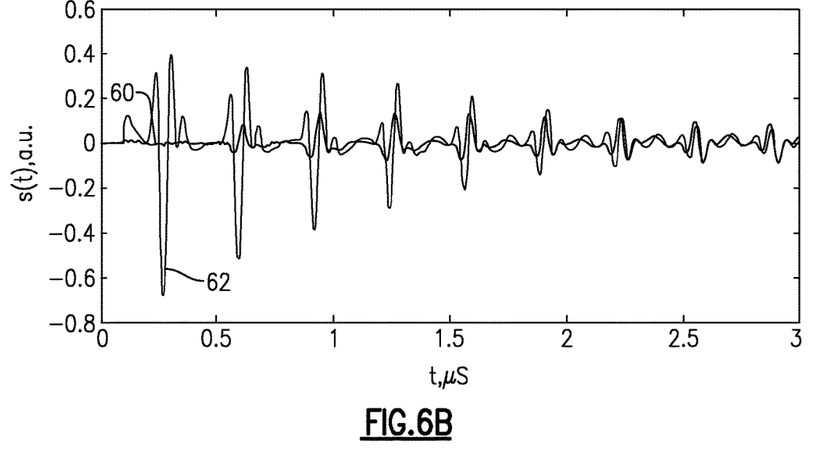
FIG. 6B shows the experimental waveforms (grey curves) measured for the joint.

FIGS. 6A and 6B show the experimental waveforms (grey curves) measured for the joint which consists of the steel plates 22, 24 with the thickness of $h_1=1$ mm and epoxy-based adhesive 26. FIG. 6 shows the waveforms s(t) (grey lines 62) and $s_2(t) \approx s(t) - s_R(t)$ (black lines 60). FIG. 6A illustrates a good joint and FIG. 6B illustrates a defect 32, 33 (FIG. 1). Thickness of the adhesive 26 (FIG. 1) is 0.4 mm. The reflection coefficient was estimated to be $|R_{12}| \approx 0.9$. The results of subtraction of the estimated response $s_1(t)$ from the initial waveforms give the residual which can be treated as a response $s_2(t) \approx s(t) - s_{R2}(t)$. The estimated responses $s_2(t)$ are presented in FIG. 6 as black lines 60. The polarity of $s_2(t)$ is coincide with the polarity of the initial waveform in case of the good joint (graph A) whereas the polarity of $s_2(t)$ is inversed in case of the disbond at the second adhesive/second plate interface (graph B) This inversion takes place due to negative value of the reflection coefficient at the rear adhesive/air interface in presence of the disbond.

Figure 7:
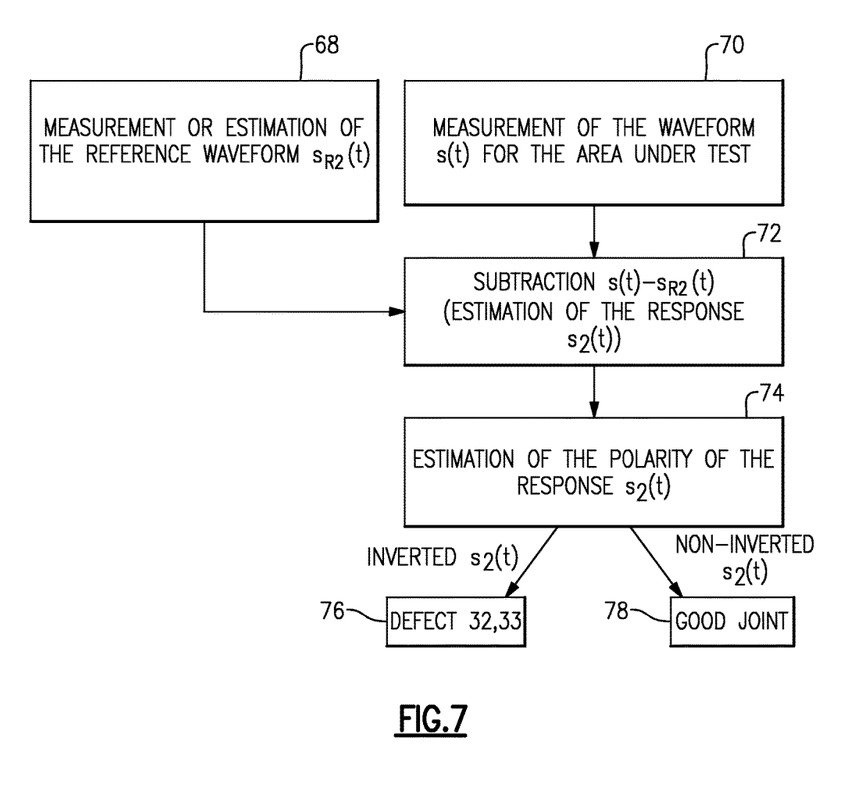
FIG. 7 shows the block-scheme of the processing algorithm for detection defects #2, 3.

FIG. 7 shows the block-diagram of the processing algorithm for detection of defects 32, 33 (FIG. 1). The reference waveform $s_{R2}(t)$ is measured or estimated in step 68. The waveform under test s(t) is measured in step 70. The response $s_2(t)$ is estimated as $s(t) - s_{R2}(t)$ in step 72. The polarity of $s_2(t)$ is estimated in step 74. If the polarity of $s_2(t)$ is inverted, there is determined to be a defect 32 or 33 in step 76. If the polarity of $s_2(t)$ is non-inverted, it is determined to be a good joint in step 78.

The robustness of the defect detectability depends on many factors including curvature and roughness of the surfaces, variations of the thickness of the plates and the adhesive layer, non-stability of the acoustical contact between the transducer and the sample. These factors cause the time shift of the recorded waveform, decreasing of its amplitude and changes in the period of the reverberations in the first plate. As the result the divergence between the reference signal and the responses $s_1(t)$ of the measured waveforms increases and the accuracy of the estimation of the response $s_2(t)$ decreases. To compensate for the time shift and overall amplitude variation, the time delay and amplitude of the first pulse reflected at the transducer-plate interface were measured and then the waveforms is normalized in amplitude and aligned in time domain. The influence of this thickness variation can be reduced by recording the reference signal in the vicinity of the testing point. This, however, is not always possible due to restricted access to the joint; neither is frequent repetition of this setup procedure convenient in the case of long joints.

Figure 8:
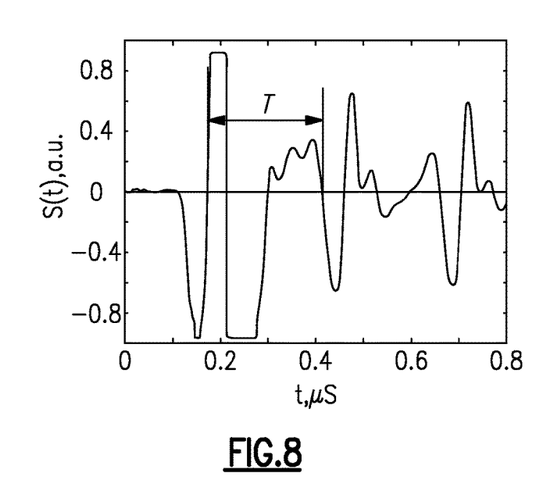
FIG. 8 shows an estimation of the period of the ultrasound reverberations in the first plate.

FIG. 8 shows an estimation of the period of the ultrasound reverberations in the first plate. To compensate variations in the reverberation period, it is proposed that after amplitude normalization and time alignment the waveforms be scaled in the time domain by $T_0/T$, where T and $T_0$ are the periods of reverberations for the measured waveform and reference signal, respectively. To avoid interference caused by the echoes from the adhesive and second metal layers, the period T is measured as the time delay between the leading fronts of the pulses reflected at the front and rear surfaces of the first plate (FIG. 8).

The proper threshold value $r_0$, time gate $[t_1, t_2]$, damping coefficient $R_{12}$, and other parameters which used in the proposed technique can be optimized by comparing the ultrasonic data and the results of the destruction test of a set of samples. Alternatively a set of specially prepared calibration samples can be used (FIG. 9).

Figure 9:
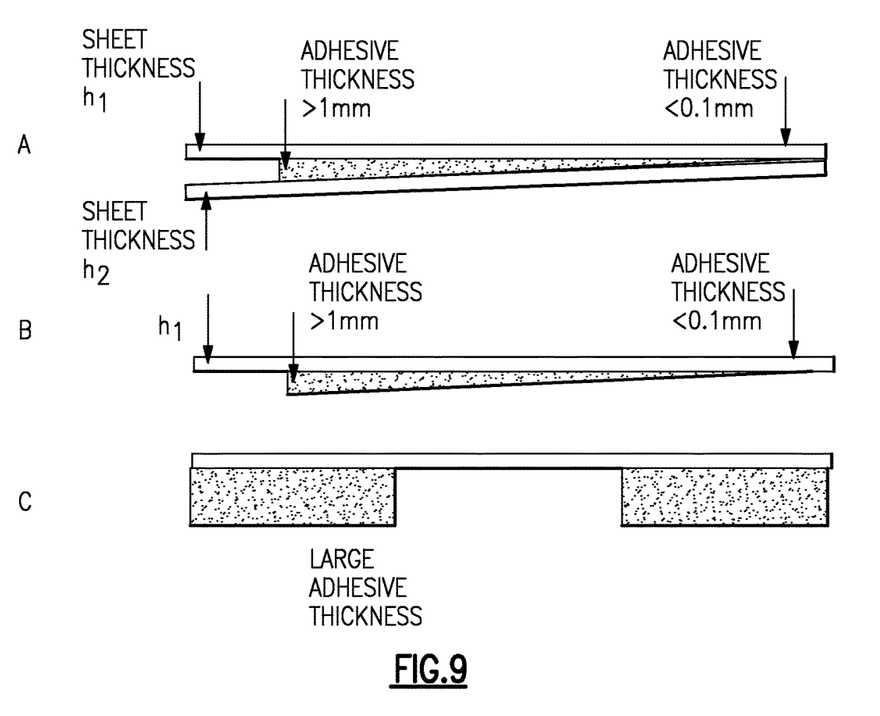
FIG. 9 shows a set of calibration samples.

FIG. 9 shows a set of calibration samples. The calibration samples A and B have the gradually varying thickness of the adhesive layer and the thicknesses $h_1$, $h_2$ and material identical to those of the parts which should be tested. The s(x,t) data recorded as a function of the time t and longitudinal position of the transducer x cover almost all possible thicknesses of the adhesive layer h at given thicknesses of the plates $h_1$, $h_2$. An example of the s(x,t) data is shown in FIG. 4.

The calibration sample C has area with very thick adhesive. The waveform measured at this area can be used as estimation of the reference waveform $s_{R2}(t)$ or can be used for adjustment of the damping parameter $R_{12}$.

Figure 10:
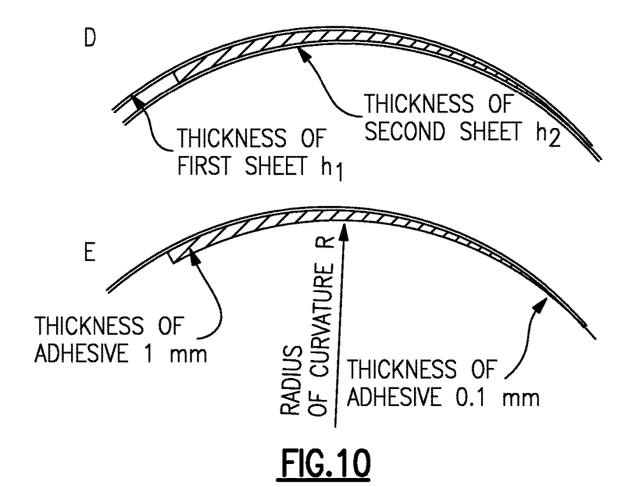
FIG. 10 shows curved calibration samples.

FIG. 10 shows curved calibration samples. Using curved calibration samples as shown in FIG. 10 it is possible to determine how the output of the processing varies with the curvature of the specimen and knowing this established relationship and the curvature of the sample under the test it is possible to adjust the output parameter and increase the detectability of defects.

The technique presented above can be applied for the testing of the small area of the sample which is approximately equal to the dimension of the interrogating ultrasound beam. Also it is applicable in the cases when the testing is produced by means of manual or robotic translation of the probe or by means of electronic switching of elements of multi-element ultrasonic probe to generate B- or C-scans.

Second Approach

This approach should be used when the adhesive has highly non-flat adhesive/air interface within the transverse dimension of the interrogating ultrasonic beam (foam-like defect) or adhesive has approximately flat interface inclined with respect to the surfaces of the plates or when the first and second sheets are not parallel.

Figure 11:
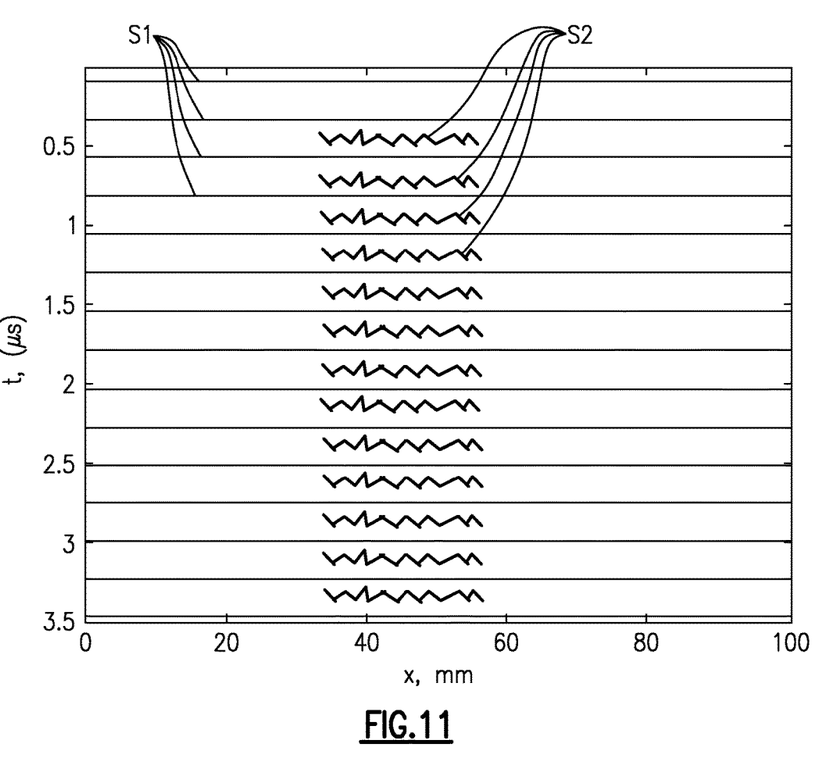
FIG. 11 shows the structure of the s(x,t) data recorded for the sample with defect #4.
Figure 12:
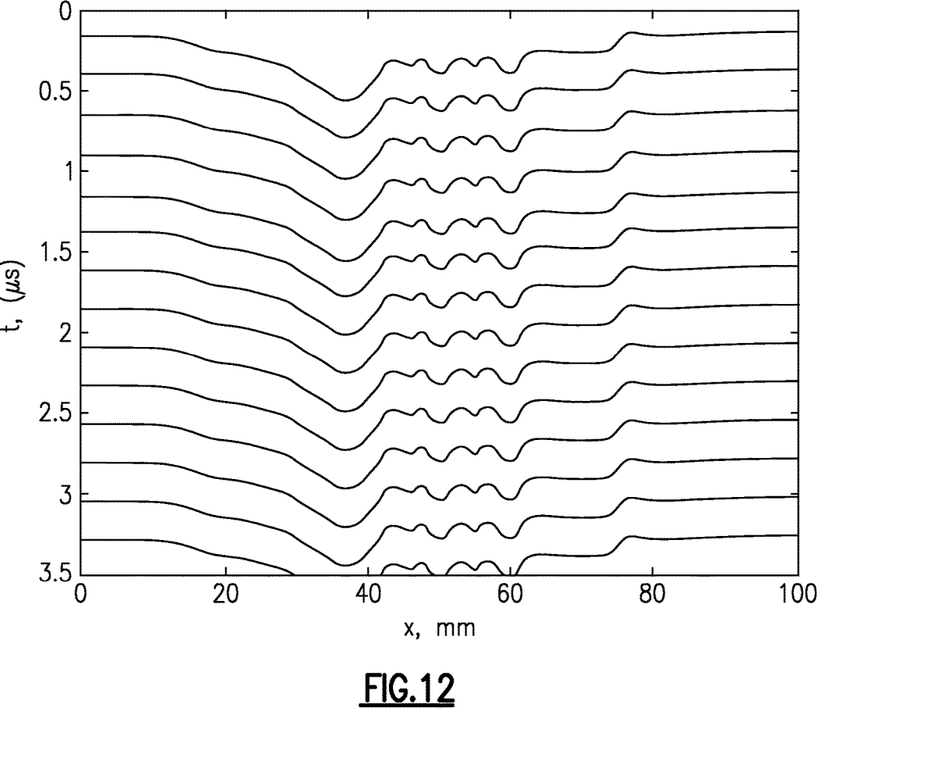
FIG. 12 shows the structure of the s(x,t) data presented in FIG. 11 after high frequency filtration over x.

FIG. 11 shows the structure of the s(x,t) data recorded for the sample with foam-like defect #4 produced by presence of air bubbles and channel in the adhesive. In the joint there are the steady response S1 and the weak response S2 which time delay and amplitude are not regular. It is possible to detect the response S2 applying a high frequency filtration of the s(x,t) data over the spatial coordinate x (FIG. 12). Similar, it is possible to detect the response S2 in cases when the rear surface of the adhesive layer is flat but substantially not parallel to the first plate. In these cases the inversion of the polarity of the selected response S2 can be used as an evidence of the void presence.

For a good joint and for relatively large defects 31, 32, 33 the responses S1 and S2 are slowly varying functions over x and the output of the spatial high pass filter is small.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

What is claimed is:

1. A method for assessment of quality of an adhesively-bonded lap joint, the joint including a first curved metal plate, a second curved metal plate and an adhesive, the method including the steps of:
   a) sending ultrasonic waves normally to the surface of a sample outside of the joint, where the sample has a first sample curved metal plate with the same properties as does the first curved metal plate at an assessment point of the joint, and wherein the sample has a second sample curved metal plate with the same properties as does the second curved metal plate, and wherein the sample has an adhesive having a thickness that varies along the sample;
   b) recording reflected waves from the sample as a reference waveform;
   c) sending wideband ultrasonic waves normally to the surface of the joint at an assessment point;
   d) recording reflected waves of the ultrasonic waves from the joint;
   e) analyzing a waveform of the reflected waves from the joint and reference waveform to determine an informative parameter; and
   f) comparing the informative parameter with a threshold value to assess quality of the joint.

2. The method of claim 1, wherein the informative parameter is a measure of the deviation of the waveform reflected from the joint and the reference waveform.

3. The method of claim 2 further including the step of determining a defect is present based upon a determination that the deviation of the waveform from the joint and the reference waveform is below a threshold.

4. The method of claim 1, further including the step of multiplying the reference waveform with an exponentially decaying function having specific exponential factor and subtracting the product from the waveform recorded from the joint to obtain a difference.

5. The method of claim 4 further including the step of monitoring polarity of the difference to obtain an indication of the defect in the joint.

6. The method of claim 1 further including the step of compensating for time shift, overall amplitude variation and variation of a reverberation period of the waveform.

7. The method of claim 1 further including the step of translating a transducer along a surface of the joint and generating an image map of the quality of the joint.

8. The method of claim 7 further including the step of high pass filtering the image map and monitoring a level of irregular output to determine a presence of a foam-like defect.

9. The method of claim 1 where the sample has a first sample metal plate with properties similar to the first metal plate at the assessment point of the joint.

10. The method of claim 1 where the sample is a portion of the first metal plate outside the joint.

* * * * *